(12) United States Patent
Ambrosen et al.

(10) Patent No.: US 7,670,998 B2
(45) Date of Patent: Mar. 2, 2010

(54) SOLID HAIR CONDITIONING PRODUCT

(75) Inventors: Helen Ambrosen, Dorset (GB); Mark Constantine, Dorset (GB); Margaret Constantine, Dorset (GB)

(73) Assignee: Cosmetic Warrior Limited, Poole, Doreset (GB)

( * ) Notice: Subject to any disclaimer, the term of this patent is extended or adjusted under 35 U.S.C. 154(b) by 1368 days.

(21) Appl. No.: 10/501,199

(22) PCT Filed: Jan. 13, 2003

(86) PCT No.: PCT/GB03/00096

§ 371 (c)(1),
(2), (4) Date: Jan. 31, 2005

(87) PCT Pub. No.: WO03/057182

PCT Pub. Date: Jul. 17, 2003

(65) Prior Publication Data

US 2006/0188460 A1    Aug. 24, 2006

(30) Foreign Application Priority Data

Jan. 11, 2002    (GB) ................. 0200601.3

(51) Int. Cl.
*C11D 3/382* (2006.01)
*C11D 3/44* (2006.01)
*C11D 1/12* (2006.01)

(52) U.S. Cl. .............. 510/127; 510/119; 510/120; 510/130; 510/133; 510/141; 510/146; 510/438; 510/440; 510/462; 510/463

(58) Field of Classification Search .......... 510/119, 510/120, 127, 130, 133, 141, 146, 438, 440, 510/462, 463
See application file for complete search history.

(56) References Cited

U.S. PATENT DOCUMENTS

| 3,932,614 | A | * | 1/1976 | Scott ................... 514/772.6 |
| 4,012,341 | A |   | 3/1977 | Orshitzer et al. ............ 252/548 |
| 4,017,574 | A | * | 4/1977 | Joshi ..................... 510/146 |
| 4,344,446 | A |   | 8/1982 | Ehrhardt |
| 4,360,387 | A | * | 11/1982 | Brown et al. ............. 106/243 |
| 4,742,083 | A | * | 5/1988 | Ritchey ................. 514/617 |
| 4,919,838 | A |   | 4/1990 | Tibbetts et al. ............ 252/117 |
| 4,941,990 | A | * | 7/1990 | McLaughlin ............. 510/151 |
| 5,578,307 | A | * | 11/1996 | Wunderlich et al. ......... 424/744 |
| 5,622,993 | A | * | 4/1997 | McGinity et al. ........... 514/626 |
| 5,648,066 | A |   | 7/1997 | Stepniewski ............... 424/64 |
| 5,849,280 | A |   | 12/1998 | Rechelbacher et al. ... 424/70.11 |
| 5,874,392 | A |   | 2/1999 | Halvorson et al. .......... 510/129 |
| 6,241,978 | B1 | * | 6/2001 | Schlaeger ................. 424/70.2 |
| 6,312,676 | B1 |   | 11/2001 | Rechelbacher et al. ... 424/70.11 |
| 6,391,373 | B1 | * | 5/2002 | Kaiser et al. ............. 426/631 |
| 2001/0007690 | A1 | * | 7/2001 | Girsh ..................... 426/442 |
| 2001/0014315 | A1 | * | 8/2001 | Harbeck .................. 424/70.2 |
| 2003/0138503 | A1 | * | 7/2003 | Staniforth et al. ........ 424/725.1 |
| 2003/0157050 | A1 | * | 8/2003 | Ambrosen et al. ............ 424/74 |
| 2005/0014825 | A1 | * | 1/2005 | Yam ...................... 514/547 |

FOREIGN PATENT DOCUMENTS

| EP | 0 330 435 | 2/1989 |
| EP | 0 823 252 | 2/1998 |
| EP | 1 108 777 | 11/2000 |
| WO | WO 00 47181 | 8/2000 |
| WO | WO 01 82889 | 11/2001 |
| WO | WO 02 47634 | 6/2002 |
| WO | WO 03 000205 | 1/2003 |

OTHER PUBLICATIONS

Patents Act 1977 Search Report under Section 17, Application No. GB 0200601.3, Date of Search Jul. 3, 2002, 2 pages.

* cited by examiner

*Primary Examiner*—Charles I Boyer
(74) *Attorney, Agent, or Firm*—Westman, Champlin & Kelly, P.A.

(57) ABSTRACT

A cosmetic product (1) for conditioning hair, the cosmetic product having the form of a solid and comprising at least one hair conditioning ingredient. Cocoa butter, cetearyl alcohol (and) sodium lauryl sulfate and glyceryl stearate (and) PEG 100 stearate are used to form the solid and the at least one hair conditioning ingredient is a known hair conditioning ingredient, such as lanolin and cetrimonium bromide. The solid cosmetic product may combined in a bar or a small shape (3) with shampoo (2).

17 Claims, 1 Drawing Sheet

SOLID HAIR CONDITIONING PRODUCT

CROSS-REFERENCE TO RELATED APPLICATION

This Application is a Section 371 National Stage Application of International Application No. PCT/GB03/00096, filed Jan. 13, 2003 and published as WO 03/057182 on Jul. 17, 2003, in English, the contents of which is hereby incorporated by reference in its entirety.

BACKGROUND OF THE INVENTION

The present invention relates to cosmetic hair conditioning products and to a method for fabricating such products.

In cosmetics, the cleansing and conditioning of the hair has been achieved by use of liquid products. Conditioning products are applied to the hair after shampooing to reduce static charge, give combability and shine. They are in a liquid state and are poured on to the hand and applied to the hair, massaged through and then rinsed away.

One conventional liquid hair conditioning product has the following formulation:

|  | % by weight |
| --- | --- |
| Water | 91.0 |
| Methyl Paraben | 0.2 |
| Propylene Glycol | 5.0 |
| Propyl Paraben | 0.1 |
| Cetearyl Alcohol (and) Sodium Lauryl Sulfate | 1.8 |
| Cetearyl Alcohol | 0.7 |
| Lanolin | 0.7 |
| Cetrimonium Bromide | 0.5 |

Conditioners are conventionally supplied in containers made, for example, of a rigid or semi-rigid plastics material. Usually, this involves the use of a plastic container and cap to contain the product. In use the bottle may break, particularly when travelling. The container has to be disposed of after use and adds to the environmental impact packaging makes. Thus, the container adds significantly to the cost of the product and environmental pollution is caused by the disposal of empty containers.

In addition, conventional conditioners require preservatives to prevent the growth of microorganisms therein. However, such preservatives have the disadvantages of irritating users' skin and reduced biodegradability.

There is an increasing awareness of environmental issues particularly with regard to the disposal of product packaging and the like. The present invention has been made against this background.

Figure 1:
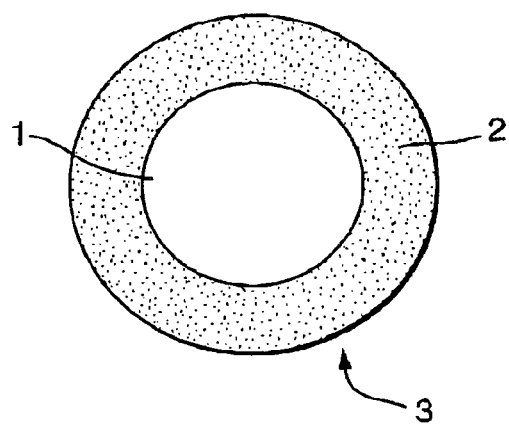
FIGS. 1, 2 and 3 show arrangement of two phases in accordance with the present invention.

According to one aspect of the present invention, there is provided a hair conditioning product, the product having the form of an emulsified solid and comprising at least one hair conditioning ingredient.

SUMMARY OF THE INVENTION

According to a further aspect of the present invention, there is provided a method of fabricating an emulsified solid form cosmetic hair conditioning product, comprising mixing a plurality of ingredients so as to provide a mixture including at least one hair conditioning ingredient, warming the mixture to a temperature within a range of from about 45° C. to about 60° C., allowing the mixture to cool, applying further mixing of the mixture when the mixture has attained a temperature within a range of from about 35° C. to about 25° C., and allowing the mixture to cool further to provide the emulsified solid form hair conditioning product.

Since the cosmetic product has the form of a solid, there is no requirement for a plastic container and there is a consequentially beneficial reduction in costs and avoidance of environmental pollution. In addition, the present invention can provide appealing novelty items.

DETAILED DESCRIPTION OF ILLUSTRSTIVE EMBODIMENTS

Embodiments of the present invention will now be described in more detail and by way of further example only, with reference to the drawings, each of which shows a cross-section of a product according to the present invention.

The present invention has been made with the intention of creating a solid conditioning product, which has the same or an improved effect on the hair as a conventional liquid formulation. It has surprisingly been found that a simple mixture of certain known hair conditioning ingredients, for example as included in the conventional liquid hair conditioning product above, together with a vegetable fat, and in particular cocoa butter, produces a relatively stable solid form product. Optionally, the cocoa butter can be used in combination with other emulsifying waxes or such waxes may be used alone. With the present invention it has also been found that with appropriate control of the process conditions, emulsification of the product ingredients can be achieved to a very high standard, even when water is present in the formulation, to provide the relatively stable solid form product.

For example, the solid conditioning product of the present invention may be formulated from materials in the following ranges:

|  | % by weight |
| --- | --- |
| Cocoa Butter | 10%-50% |
| Cetearyl Alcohol (and) Sodium Lauryl Sulfate | 6%-30% |
| Glyceryl stearate (and) PEG100 stearate | 0%-20% |
| Cetearyl Alcohol | 2%-15% |
| Cetrimonium Bromide | 0.5%-5% |
| Lanolin | 0.5%-5% |
| Propylene Glycol | 5%-30% |
| Water | 0%-25% |

The first three ingredients, namely cocoa butter, cetearyl alcohol (and) sodium lauryl sulfate, and glyceryl stearate (and) PEG 100 stearate, form the solid and help condition the hair. The remaining ingredients are core ingredients of a conventional liquid conditioner, which have been made into a solid with the addition of the emulsifying waxes. Cetearyl alcohol and sodium lauryl sulfate may be used or added separately, rather than premixed in one ingredient. Similarly, glyceryl stearate and PEG 100 stearate, which act as an emulsifying wax, may be used or added separately, rather than premixed in one ingredient.

Accordingly, a feature of the present invention is that conditioning ingredients of a conventional liquid conditioner are mixed with at least one other ingredient, preferably cocoa butter and/or emulsifying waxes, which solidify the product.

Thus, one example of a conditioning product according to the present invention may be formulated as follows:

% by weight
Cocoa Butter 25.0
Cetearyl Alcohol (and) Sodium Lauryl Sulfate 25.0
Glyceryl Stearate (and) PEG 100 Stearate 10.0
Cetearyl Alcohol 5.0
Cetrimonium Bromide 1.5
Lanolin 1.5
Propylene Glycol 27
Water 5.0
Total 100.0

The method by which the conditioning product of the present invention may be fabricated is considered to be particularly advantageous and, surprisingly, provides a very stable emulsified mixture, even when water is present at up to 25% by weight in the mixture. All of the ingredients are mixed together and the mixture is warmed to a maximum temperature of approximately 60° C. A warming temperature in the range of from about 45° C. up to about 60° C. has been found to be particularly beneficial in this respect. At this temperature the cocoa butter, and other emulsifying waxes if present, are softened, which facilitates the mixing of the ingredients but the mixture does not emulsify at this stage. The mixture is then allowed to cool from the warmed temperature, and during an initial phase of the cooling cycle, down to about 35° C., the mixing of the ingredients may be discontinued as it has been found not to provide any particular benefit in terms of the dispersion of the ingredients or emulsification in the final product. When a temperature of between about 35° C. and about 25° C. is reached during the cooling cycle, the mixing of the ingredients is recommenced. In this temperature range, efficient and very high quality emulsification of the ingredients has been found to occur, and this has also been found to be dependent on the maximum temperature to which the mixture is warmed during the initial phase of the fabrication process. A temperature in the range of from about 27° C. to about 30° C. has been found to be particularly beneficial when further mixing of the ingredients is provided.

Usually, when an emulsifying wax is used in a cosmetic product, the mixed ingredients are heated to a temperature of about 75° C. to soften the waxes and assist dispersion of the ingredients being mixed. However, it has been found with the present invention that if a temperature of 75° C. is used the subsequent dispersion and emulsification of the mixed ingredients in the resulting product is reduced and an inferior quality product is obtained. The solid form conditioning product of the present invention is therefore different to the known products of this type.

The conditioning product of the present invention is also very different to the solid form products in which particulate needle or powdered form ingredients are compacted under pressure in a mould to provide a solid form composition, sometimes using a binder material to assist in providing the solid product. Furthermore, because the ingredients can be mixed with warming only to a relatively low temperature of about 60° C. maximum, there is reduced risk that certain ingredients are not degraded as a result of the fabrication process. The fabrication process can also, therefore, be carried out simply and at lower cost, but the resulting emulsified product is of superior quality. Control of the fabrication process parameters in accordance with the present invention is considered therefore to bring particular and unexpected benefits. This particularly so when considering that a superior quality and stable emulsified product is provided, which can be cut without fragmentation but is sufficiently solid for normal handling in use of the product, and which does not require the addition of chemical preservatives or the use of packaging to prevent product degradation through the growth of microorganisms, even though up to about 25% of the total ingredients can comprise water. This is due to the very good emulsification of the product ingredients arising from the relatively low initial temperature to which the ingredients are warmed. If the conventional heating temperature of about 75° C. is used the emulsifying properties of the cocoa butter and or emulsifying waxes are significantly reduced.

From the foregoing, it can be seen that the principal ingredient of conventional liquid conditioners is water and this has the added disadvantage that lower concentrations of conditioning ingredients can be included in the conventional conditioner, so that larger volumes of conventional conditioner must be used to obtain the same conditioning effect as for a solid conditioning product in accordance with the present invention. Thus, the conventional conditioning product has the further comparative disadvantages of more expensive distribution and a correspondingly higher environmental impact.

The solid conditioning product of the present invention may have the form of a bar: it may be moulded into small shapes or it may have the form of a large cake shape. Because the composition is a cured solid product, as opposed to the solid products of compacted particulate or granular form, the product can be cut into smaller portions very easily without fragmentation of the product. In this respect the composition of the product can be compared to that of an edible cake. The use of cocoa butter is considered to be particularly advantageous because, surprisingly, the ingredients can be mixed into a paste with minimal heating, and the mixture is able to cure and harden naturally into a solid product, even when a significant proportion of water is included in the formulation. As such, the term solid product, when used in the context of the present invention, is not intended to include products of the type which are of powder or particulate composition (of any shape or size) and which are formed into a solid form by compaction under pressure in a mould, with or without the aid of a suitable binder material.

This solid system enables certain ingredients to be used without requiring chemical preservatives because the growth of micro-organisms is significantly retarded by the products solid state. It can be seen from the typical conventional liquid conditioning product formulation how different the solid conditioning formulation is in this respect. Moreover, the solid conditioning bar has the advantage of creating a greatly reduced impact on the environment as it does not require a plastic container. Visual impact can be made with large spectacular cakes of conditioner. Alternatively, small convenient individual shapes may convey to the customer the practical aspect of the product. The absence of conventional preservatives reduces the potential for irritation of the user. The biodegradability of the solid bar is also improved by the absence of preservatives.

In use, the bar is massaged directly onto the head or onto the hands, which are then used to apply conditioner to the hair. This delivers just the right amount of product for the desired effect. A larger bar can be cut or broken with the hands and thus small pieces of a solid bar of conditioning product can be broken off and used as required. To improve the cutting or breaking properties of such a bar, small amounts of water can be included in the formulation, for example up to 25% by weight and typically between 1% and 10% by weight. In this case, the above exemplary formulation will comprise between 99% and 90% by weight of the final product. Of course, such amounts of water can also be added to the small shapes if desired.

In addition, other materials such as stearic acid can be substituted for all or part of the glyceryl stearate (and) PEG 100 stearate in the formulation. As well as forming the solid, these ingredients have conditioning qualities for the hair. Other conditioning ingredients such as soya lecithin can be substituted for conditioning ingredients like lanolin. Herbs, fruits and/or vegetables can be combined to give different qualities to the final formulation and can vary between 5% to 25% by weight of the final product. Small amounts of additives may be included, such as a fragrance and/or colorant.

One example of the relative ratios of the components is given above. These ratios and the ingredients themselves can of course be varied, the requirement being only that a useable solid form hair conditioning product results.

Liquid formulations of shampoo with conditioning properties have been in existence for some years. However, a solid form of this type of product is hitherto unknown. A solid shampoo formulation with the solid conditioning bar formulation can be combined to create a bar having the effect of washing and conditioning the hair in one application without requiring the use of two separate products. This has all the advantages of the conditioning bar, including no packaging and no preservatives. Similarly, the shampoo and conditioning bar of the present invention can be moulded into small individual shapes or large cakes which can be cut into individual portions.

The proportion of shampoo material compared to the amount of conditioning material is variable. Dry hair would benefit from a greater amount of conditioner. Flat, fine hair would be washed and conditioned more successfully with a smaller proportion of conditioner to shampoo material.

A basic proportion of 50:50 shampoo to conditioner is given in the following example. However, this proportion may have the range of 30-70% by weight of conditioner and 70-30% by weight of shampoo.

Example of a Shampoo and Conditioning Bar

|  | % by weight |
|---|---|
| Shampoo | |
| Sodium Lauryl Sulfate | 48.5 |
| Cocamide D.E.A. | 1.5 |
| Conditioner | |
| Cocoa Butter | 12.5 |
| Cetearyl Alcohol (and) Sodium Lauryl Sulfate | 12.5 |
| Glyceryl Stearate (and) PEG 100 Stearate | 5.0 |
| Cetearyl Alcohol | 2.5 |
| Cetrimonium Bromide | 0.75 |
| Lanolin | 0.75 |
| Propylene Glycol | 13.5 |
| Water | 2.5 |
| Total | 100.0 |

The range of percentages for this type of product reflects the proportion of shampoo to conditioner. However, the proportion of ingredients in the conditioner varies in the same way as in the conditioning bar.

Ideally, the distribution of the conditioner and the shampoo in the bar enables the user to apply both to the hair at the same time. The arrangement of the two phases may be as shown in FIGS. 1 to 3, each of which shows a shape 3 of solid shampoo and conditioner.

Figure 2:
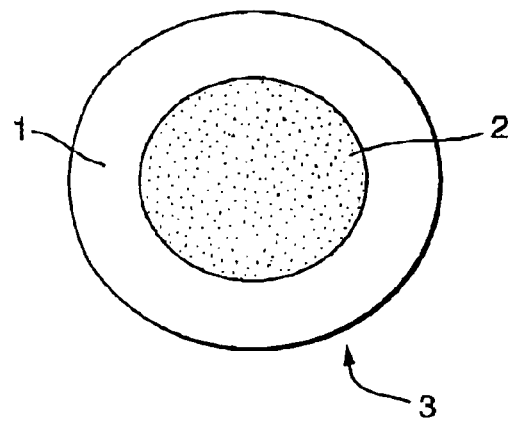
Figure 3:
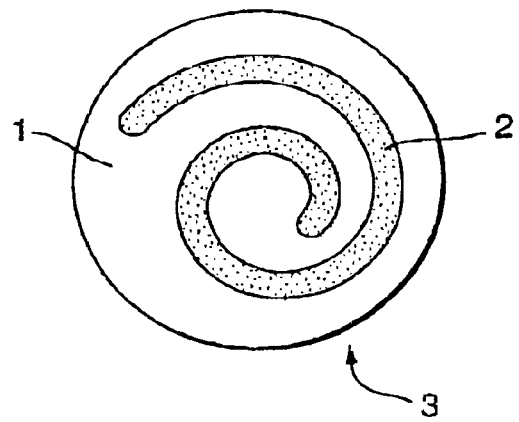

As FIGS. 1 and 2 show, the shampoo 2 or alternatively the conditioner 1 can form the middle of the bar 3. As FIG. 3 shows, patterns such as a spiral may be formed through the bar with one or the other of the phases. It is also possible to merge the two formulations together to form a homogenous mixture. The bars may be in small individual shapes or large cakes which can be cut into smaller portions.

Of course the general aesthetic appeal and marketing possibilities of such a combined solid shampoo and conditioning product, as well as the other features, are the same as for the solid conditioning product alone.

The aforegoing description has been given by way of example only and it will be appreciated by a person skilled in the art that modifications can be made without departing from the scope of the present invention as defined by the appended claims.

The invention claimed is:

1. A cosmetic hair conditioning product, the product having the form of an emulsified solid composition and comprising at least one hair conditioning ingredient and a principle solidifying ingredient comprising:
   a) from 10% to 50% by weight of the product of cocoa butter; and
   b) from 6% to 37% by weight of the product of a mixture of cetearyl alcohol and sodium lauryl sulfate.

2. A cosmetic product according to claim 1 further comprising a solidifying ingredient selected from the group consisting of glyceryl stearate, PEG 100 stearate and stearic acid, or mixtures thereof.

3. A cosmetic product according to claim 2, prepared from a mixture including up to 20% by weight of at least one of glyceryl stearate, PEG 100 stearate and stearic acid.

4. A cosmetic product according to claim 1, wherein one solidyfing ingredient is also a hair conditioning ingredient.

5. A cosmetic product according to claim 1, wherein the at least one conditioning ingredient comprises at least one of propylene glycol, cetearyl alcohol, sodium lauryl sulfate, lanolin, soya lecithin and cetrimonium bromide.

6. A cosmetic product according to claim 1, further comprising up to 25% by weight of water.

7. A cosmetic product according to claim 1, further comprising 5% to 25% by weight of at least one of herbs, fruits and vegetables.

8. A solid hair treatment product, comprising a shampoo and a cosmetic product according to claim 1.

9. A solid hair treatment product according to claim 8, comprising 30% to 70% by weight of the shampoo and 70% to 30% by weight of the cosmetic product.

10. A solid hair treatment product according to claim 8, wherein the cosmetic product is surrounded by the shampoo.

11. A solid hair treatment product according to claim 8, wherein the shampoo is surrounded by the cosmetic product.

12. A solid hair treatment product according to claim 8, wherein the cosmetic product and the shampoo form a pattern.

13. A solid hair treatment product according to claim 12, wherein the pattern is arranged to enable contemporaneous application of the cosmetic product and the shampoo to the hair of a user.

14. A solid hair treatment product according to claim 13 wherein the pattern comprises a spiral pattern.

15. A method of fabricating an emulsified solid form cosmetic hair conditioning product according to claim 1, comprising mixing the at least one hair conditioning ingredient and the principle solidifying ingredient, warming the mixture to a temperature within a range of from 45° C. to 60° C., allowing the mixture to cool, applying further mixing when the mixture has attained a temperature within a range of from 35° C. to 25° C., and allowing the mixture to cool further to provide the emulsified solid form hair conditioning product.

16. A method according to claim 15 wherein the further mixing is provided when the mixture has attained a temperature of between 27° C. and 30° C.

17. A method according to claim 15 wherein the product further comprises water up to 25% by weight of the mixture.

* * * * *